United States Patent
Critz

(10) Patent No.: US 7,234,308 B1
(45) Date of Patent: Jun. 26, 2007

(54) COLD MOLD

(76) Inventor: Carl H. Critz, 24 Tea Tree Ct., Danville, CA (US) 94526

( * ) Notice: Subject to any disclaimer, the term of this patent is extended or adjusted under 35 U.S.C. 154(b) by 263 days.

(21) Appl. No.: 10/952,583

(22) Filed: Sep. 29, 2004

(51) Int. Cl.
*F25B 19/00* (2006.01)
*F25D 25/00* (2006.01)
*F25C 1/00* (2006.01)
*B22D 15/00* (2006.01)
*B22C 9/20* (2006.01)
*B28B 7/24* (2006.01)
*B28B 7/34* (2006.01)
*B28B 7/28* (2006.01)

(52) U.S. Cl. ............... 62/51.1; 62/62; 62/66; 249/111; 249/119; 249/135; 249/177

(58) Field of Classification Search ........... 62/51.1, 62/62, 66; 249/111, 119, 123, 135, 177
See application file for complete search history.

(56) References Cited

U.S. PATENT DOCUMENTS

| | | | | |
|---|---|---|---|---|
| 2,868,072 A * | 1/1959 | Weiskopf et al. | ............... | 269/7 |
| 2,996,762 A | 8/1961 | McCormick | | |
| 3,204,424 A | 9/1965 | McCormick et al. | | |
| 3,218,896 A | 11/1965 | McCormick | | |
| 3,234,595 A * | 2/1966 | Weichselbaum et al. | .... | 425/117 |
| 3,261,600 A * | 7/1966 | Horn | ............ | 269/277 |
| 3,411,185 A | 11/1968 | Pickett | | |
| 3,667,330 A * | 6/1972 | Kobernick | ............ | 83/98 |
| 3,674,396 A | 7/1972 | McCormick | | |
| 5,452,584 A | 9/1995 | Diggs | | |
| 5,533,342 A | 7/1996 | Gordon | | |
| 5,550,033 A * | 8/1996 | Krumdieck | ............ | 435/40.52 |
| 5,776,298 A | 7/1998 | Franks | | |
| 5,782,572 A | 7/1998 | Thiem | | |
| 5,817,032 A | 10/1998 | Williamson, IV et al. | | |
| 5,829,256 A | 11/1998 | Rada | | |
| 6,017,476 A | 1/2000 | Renshaw | | |
| 6,289,682 B1 | 9/2001 | Rada | | |
| 6,387,653 B1 | 5/2002 | Voneiff et al. | | |
| 6,536,219 B2 * | 3/2003 | Peters | ............ | 62/62 |
| 2005/0112034 A1 * | 5/2005 | McCormick | ............ | 422/102 |
| 2005/0247068 A1 * | 11/2005 | Marsing et al. | ............ | 62/62 |

* cited by examiner

*Primary Examiner*—William C. Doerrler
(74) *Attorney, Agent, or Firm*—John P. McGonagle

(57) ABSTRACT

A metallic, reusable mold with one or more wells. The mold is kept within a cryostat at low temperature. The mold is removed from the cryostat and a tissue specimen is placed into a well within the mold. An embedding medium is added to the well around the tissue specimen. A pre-chilled chuck is then placed against the well opening. The mold with tissue specimen, embedding medium and chuck are returned to the cryostat and the specimen is frozen into a block. The mold and contents are removed and hot water poured against the mold releasing the block with attached chuck from the well. The chuck with attached block is then available for sectioning or other processing.

8 Claims, 3 Drawing Sheets

COLD MOLD

BACKGROUND OF THE INVENTION

This invention relates generally to the preparation of tissue specimens, and in particular to forming and freezing tissue specimens while preserving a desired orientation of the specimen.

Various disease processes, particularly tumors, require a histologic diagnosis. Preparation of tissue specimens for rapid histological examination requires the preservation of the integrity and spatial positioning of the tissue specimen. Tissue integrity and spatial positioning relative to the eventual cutting plane of a microtome are important for histological evaluation of the appropriate areas and their relationship to margins and other structures. If the relevant areas of the tissue do not lie on the same plane, then several sections of the tissue must be taken and made into separate slides for evaluation. Each of these different slides will have a different part of the original tissue sample and will need to be separately evaluated by the pathologist. Pathologic examination can be significantly improved and the cost reduced if a single slide of the tissue can include all of the relevant areas that need evaluation in the biopsy including the abnormal tissue and the margins.

Biopsy, or surgical removal of a tissue specimen for histologic examination, is frequently employed in order to establish a precise diagnosis. When a lesion is known or suspected to be malignant, the entire mass is typically excised, if possible, and a rapid examination technique is often employed to determine tumor relationship to margins. In some circumstances to be effective, the technique of tumor margin surface area examination must include microscopic examination of the entire surface margin of the excised specimen. Moreover, the anatomical orientation of the tissue must be maintained throughout the procedure so that the surgeon may be directed back to a specific area of the biopsy site to excise additional tissue until histologic examination indicates that only healthy cells remain. Frozen section examination requires that the tissue first be prosected and oriented, hard frozen, and then sliced into extremely thin sections for microscopic examination.

In order to speed the examination process, the specimen must be quickly frozen to a predetermined temperature, mounted on a microtome chuck which will permit the frozen tissue to be thin sliced in a cryostat/microtome. The invention allows more precise orientation of larger, non-planar specimens, faster than current methods.

Prior art methods for freezing tissue with a desired orientation, include direct placement of the tissue sample on a cryostat chuck, placement of a freezing gel on the tissue sample, and using the cryostat anvil to apply a freezing temperature to the tissue sample. Another method is the use of a disposable plastic mold. The tissue and an aqueous solution are placed in a plastic mold. The mold and contents are then frozen within a cryostat. In both prior art methods, it is difficult to keep the tissue sample in a desired orientation. Furthermore, the plastic mold provides some heat insulation and will delay the specimen freezing process.

The apparatus and method of the present invention are specifically designed to quickly form and freeze a tissue specimen into a desired frozen block, while preserving a desired orientation of the specimen.

SUMMARY OF THE INVENTION

The present invention provides a metallic, reusable mold with one or more wells. The mold is kept within a cryostat at low temperature. The invention mold is removed from the cryostat and a tissue specimen is placed into a well within the mold. Because the invention mold is already at a low temperature, the tissue specimen will stick to the well face(s) and maintain a desired orientation. An embedding medium, such as sold under the brand name, O.C.T. COMPOUND, is then added to the well around the tissue specimen. A pre-chilled chuck is then placed against the well opening in contact with the O.C.T. liquid. The back of the chuck may be sprayed with a freezing compound. The pre-chilled mold and freezing spray can freeze the specimen rapidly with or without returning to the cryostat. Frozen blocks can be released from round molds simply by twisting the chuck and mold in opposite directions. To release rectangular blocks, hot water is poured against the mold releasing the block with attached chuck from the well. The chuck with attached block is then available for sectioning or other processing.

There are several advantages of the present invention over the prior art. A specific tissue orientation can be maintained. Because of the thermal properties of the invention mold, the tissues and solution freeze much more quickly, i.e., in 10 to 15 seconds. This compares to 2 to 3 minutes for plastic molds. The geometry of the tissue block is the same each time and is always parallel to the face of the chuck. Also, the sample is always the same size because of well depth. The present invention speeds up the production of specimen slides.

These together with other objects of the invention, along with various features of novelty which characterize the invention, are pointed out with particularity in the claims annexed hereto and forming a part of this disclosure. For a better understanding of the invention, its operating advantages and the specific objects attained by its uses, reference should be had to the accompanying drawings and descriptive matter in which there is illustrated a preferred embodiment of the invention.

DETAILED DESCRIPTION OF THE INVENTION

Figure 1:
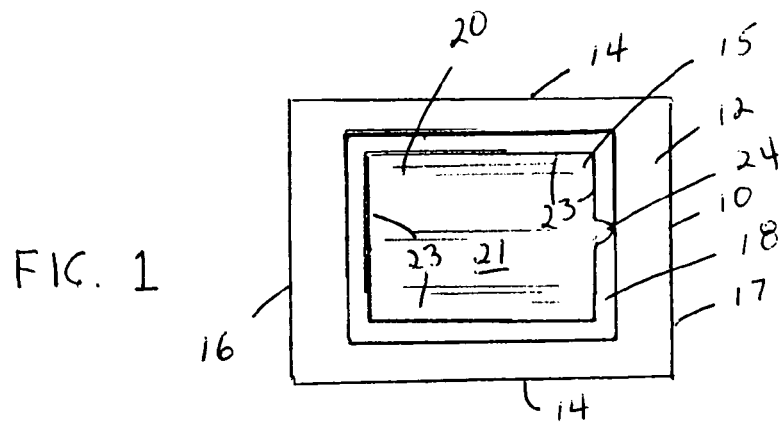
FIG. 1 is a top view of a cold mold.
Figure 2:
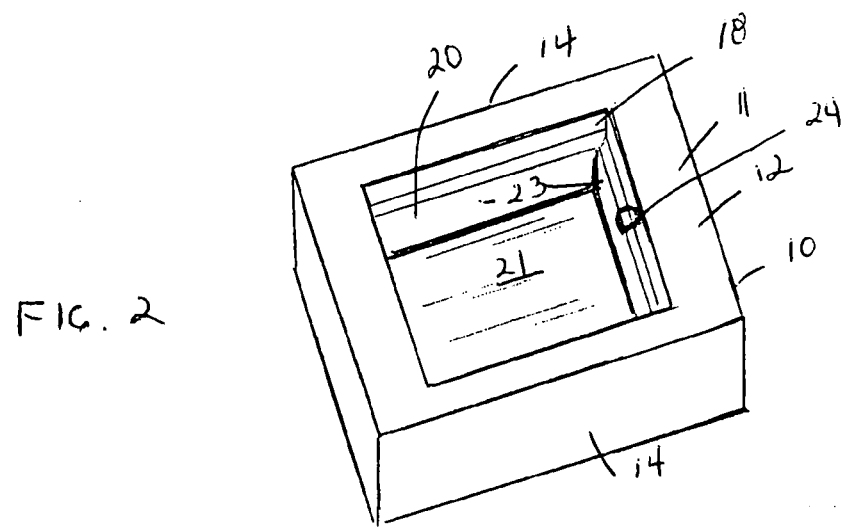
FIG. 2 is a top perspective view of a cold mold.
Figure 3:
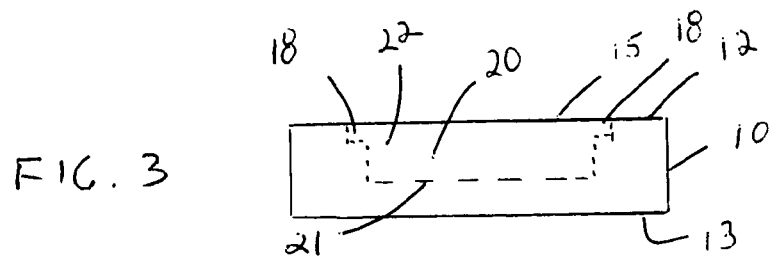
FIG. 3 is a side view of a cold mold.
Figure 4:
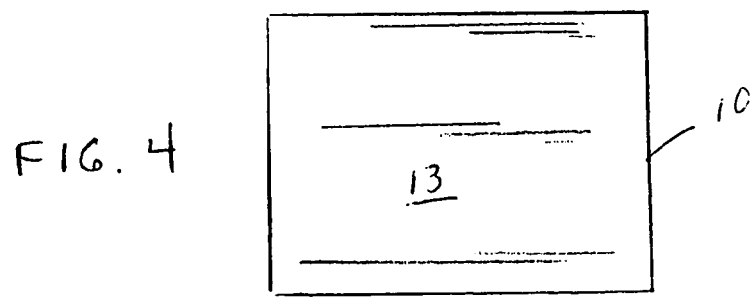
FIG. 4 is a bottom view of a cold mold.
Figure 5:
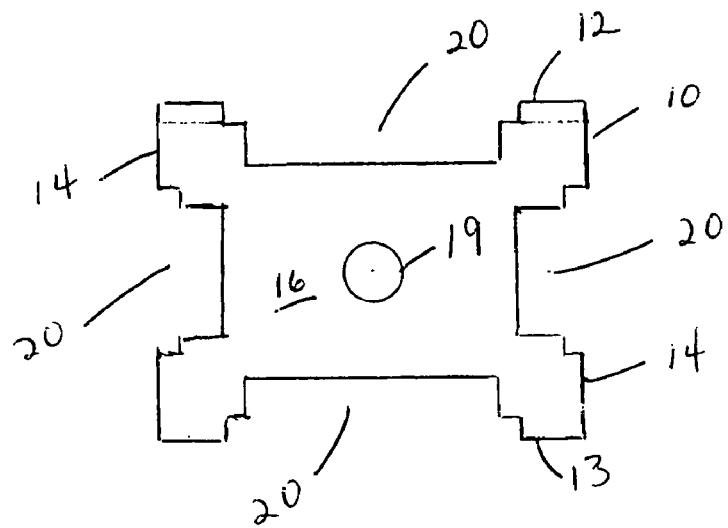
FIG. 5 is a cross sectional view of another embodiment of the cold mold.
Figure 6:
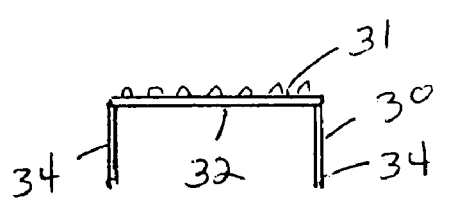
FIG. 6 is a front view of a rectangular chuck.
Figure 7:
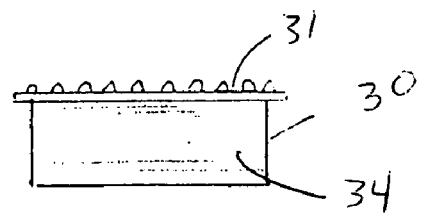
FIG. 7 is a side view thereof.
Figure 8:
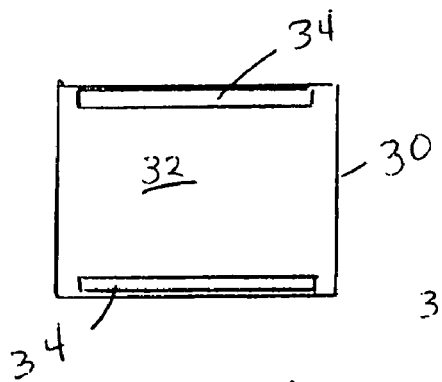
FIG. 8 is a bottom view thereof.
Figure 9:
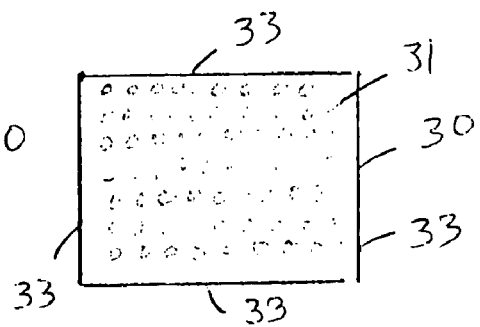
FIG. 9 is a top view thereof.
Figure 10:
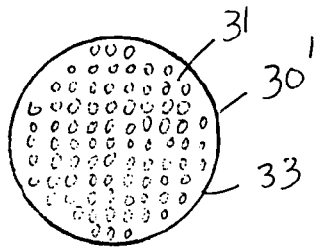
FIG. 10 is a top view of a circular chuck.
Figure 11:
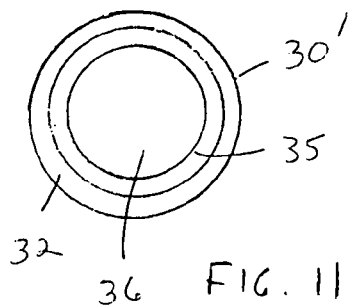
FIG. 11 is a bottom view thereof.
Figure 12:
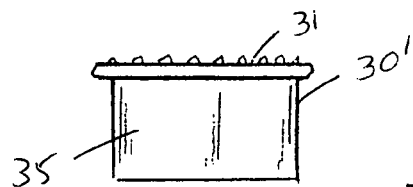
FIG. 12 is a side view thereof.
Figure 13:
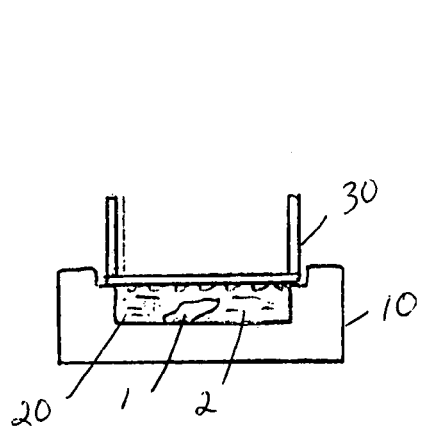
FIG. 13 is a cross sectional view of the cold mold, with tissue specimen and chuck.
Figure 14:
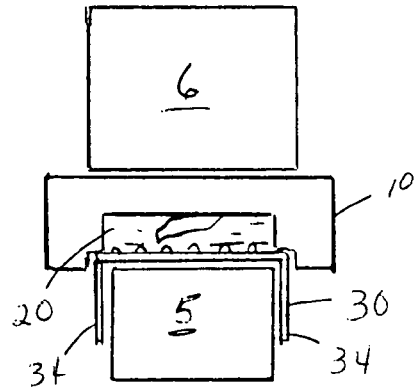
FIG. 14 is a cross sectional view of the cold mold, tissue specimen and chuck of FIG. 13, inverted and installed in a cryostat.
Figure 15:
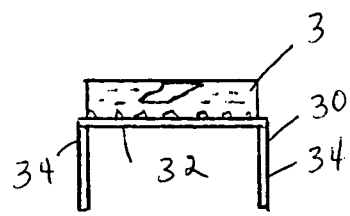
FIG. 15 is a side view of the tissue specimen block attached to a chuck.

Referring to the drawings in detail wherein like elements are indicated by like numerals, there is shown a mold 10 constructed according to the principles of the present invention. The mold 10 has an external surface 11, a top 12, a bottom 13, a front 16, a rear 17, two opposing sides 14, an opening 15 in said top 12, a well 20 formed within said mold 10 and terminating in said top opening 15. The top opening 15 has a channel 18 circumferentially formed about a top opening portion 22 of the well 20. The well 20 has a floor 21, an open top 22, and side walls 23, said side walls determining the depth of the well 20. The well 20 may also have one or more channels 24 formed in the side walls 23 and floor 21 to provide an interconnected relief channel to release surplus O.C.T. compound. The well side walls 23 may have a five degree vertical angle to promote release of the tissue specimen block 3 from the well 20. In other embodiments the surface finish of the side walls 23 and floor 21 could change the adhesion properties of the tissue specimen 1 or the releasability of the tissue specimen block 3 after freezing. Alternatively, various coatings could be applied to the side walls 23 and floor 21.

In other embodiments of the invention, the mold well 20 may have different shapes, such as rectangular, round, trapezoidal, etc. The mold 10 may also have one or several wells 20. The mold 10 may have one or more wells 20 formed with access from the mold top 12 and one or more wells 20 with access from the mold bottom 13. The mold 10 may also have one or more wells 20 formed with access from the mold top 12, bottom 13, front 16, rear 17 and sides 14. The mold 10 may also have a center hole 19 formed therein to run warm water through to warm the mold and release the frozen specimen blocks. The mold 10 is made from metal for thermal characteristics, i.e., metal being superior to plastic regarding thermal conductivity. Stainless steel will provide substantial thermal mass. However, aluminum, with less thermal mass, may be more forgiving in changing the orientation of the tissue sample. Different metals with different specific heat and thermal conductivity will allow molds with different characteristics.

There is also shown two embodiments of a chuck 30, 30' each having a planer top 31 and opposing bottom 32. The chuck may be rectangular 30 or round 30'. The rectangular chuck 30 has four sides 33 and two flanges 34 projecting downwardly from the chuck bottom 32, one flange from one side and the other flange from an opposite side. The round chuck 30' has a round side 33 and a hollow cylinder 35 projecting downwardly from the chuck bottom 32 and terminating in an open cylinder bottom 36. Some round chucks have a metal button instead of an open cylinder on the bottom for affixing the chuck to the microtome.

The chuck top 31 has a number of corrugations 35 thereon, said corrugations allowing the chuck to have a better grip on the specimen block. The chuck top 31 will have dimensions less than the dimensions of the mold top channel 18. The mold top channel 18 permits the chuck 30 to be located to the mold well top 22.

The invention is used in conjunction with a cryostat. Cryostats are well known in the art and, in their most basic form, are comprised of a cold rail 5 with a top anvil 6 and a microtome (not shown). When an object is placed on the cold rail 5 and the anvil 6 is applied to the object, freezing occurs. The method of the invention involves the following operations. The mold 10 is kept within the cryostat at low temperature. When needed, the "cold" mold 10 is removed from the cryostat and a tissue specimen 1 is placed into the cold mold well 20 on the well floor 21. Since the cold mold 10 is very cold, the tissue specimens 1 will stick to the well floor 21 in a desired position. Alternatively, a cryogenic gel may be placed in the well 20 for positioning the tissue specimen. An embedding medium 2, such as sold under the brand name, O.C.T. COMPOUND, is then added to the well 20 surrounding the tissue specimen 1. A pre-chilled chuck 30 is then placed against the well top opening 22. The chuck 30 may be chilled by applying a freeze spray to the chuck top 31. The cold mold 10 with tissue specimen 1, embedding medium 2 and chuck 30 are brought back to the cryostat, inverted and placed into the cryostat, wherein the chuck 30 is placed on the cold rail, the chuck flanges 34 or cylinder 35 holding the chuck 30 and mold 10 in place on the cold rail 5. The cryostat anvil 6 is then brought into contact with the cold mold bottom 13, wherein the tissue specimen 1 and embedding medium 2 are quickly frozen into a block 3. The chuck 30 and mold 10 are removed from the cryostat and hot water poured against the mold bottom 13 releasing the block 3 with attached chuck 30 from the cold mold well 20. Round blocks can be removed from the mold by twisting the chuck and mold in opposite directions. The cold mold 10 is cleaned and returned to the cryostat for temperature maintenance. The chuck 30 with attached block 3 is then available for sectioning or other processing.

At times the frozen tissue specimen block 3 has voids on one or more of its faces. This is easily cured by placing a few drops of the embedding medium into the void or onto a flat surface and rubbing the face to smooth the added O.C.T. compound and applying some freeze spray.

It is understood that the above-described embodiments are merely illustrative of the application. Other embodiments may be readily devised by those skilled in the art which will embody the principles of the invention and fall within the spirit and scope thereof.

I claim:

1. An apparatus for quickly forming and freezing a tissue specimen into a desired shape, while preserving a desired orientation of said tissue specimen, said apparatus adapted to be used with a cryostat having a cold rail with a top anvil, comprising:
   a pre-frozen, metallic cold mold having an external surface, a top, a bottom, a front, a rear, two opposing sides, a plurality of openings in said front, rear and opposing sides, a plurality of wells formed within said mold each terminating in a said opening, each said opening having a channel circumferentially formed about a well top opening, each said well having a floor, said well top opening, and side walls, said well side walls determining a well depth, each said well adapted to receiving a said tissue specimen and an embedding medium, each said cold mold top and bottom adapted to being engaged by said cryostat anvil;
   a pre-chilled chuck having a planar top, an opposing bottom, a plurality of sides and a plurality of flanges projecting downwardly from the chuck bottom, said chuck top having a plurality corrugations formed thereon, said chuck top adapted to fit within each said mold top channel;
   wherein the chuck is adapted to being placed on the cold rail, said chuck flanges holding the chuck in place on the cold rail.

2. An apparatus according to claim 1, further comprising:
   a center hole formed through said cold mold from top to bottom.

3. An apparatus according to claim 1, wherein:
   said chuck has four sides and two flanges projecting downwardly from the chuck bottom, one flange from one side and the other flange from an opposite side.

4. An apparatus according to claim 1, wherein:
   said chuck has a round side and a hollow cylindrical flange projecting downwardly from the chuck bottom and terminating in an open cylindrical flange bottom.

5. An apparatus for quickly forming and freezing a tissue specimen into a desired shape, while preserving a desired orientation of said tissue specimen, said apparatus adapted to be used with a cryostat having a cold rail with a top anvil, comprising:

a pre-frozen, metallic cold mold having an external surface, a top, a bottom, a front, a rear, two opposing sides, an opening in said top, a well formed within said mold and terminating in said top opening, said top opening having a channel circumferentially formed about a well top opening, said well having a floor, a said well top opening, and side walls, said side walls determining a well depth, said well adapted to receiving said tissue specimen and an embedding medium, said cold mold bottom adapted to being engaged by said cryostat anvil;

a pre-chilled chuck having a planar top an opposing bottom, a plurality of sides and a plurality of flanges projecting downwardly from the chuck bottom, said chuck top having a plurality corrugations formed thereon, said chuck ton adapted to fit within said mold top channel;

wherein the chuck is adapted to being placed on the cold rail, said chuck flanges holding the chuck in place on the cold rail; and a plurality of interconnected irrigation channels formed in said well.

6. The apparatus according to claim 5, wherein:
said well side walls are canted outward from said floor.

7. An apparatus according to claim 5, wherein:
said chuck has a round side and a hollow cylindrical flange projecting downwardly from the chuck bottom and terminating in an open cylindrical flange bottom.

8. A method for quickly forming and freezing a tissue specimen into a desired shape, while preserving a desired orientation of said tissue specimen, comprising the steps of:

pre-freezing a metallic cold mold having an external surface, a top, a bottom, a front, a rear, two opposing sides, an opening in said top, a well formed within said mold and terminating in said top opening, said top opening having a channel circumferentially formed about a well top opening, said well having a floor, a said well top opening, and side walls, said side walls determining a well depth;

placing said tissue specimen into the cold mold well on the well floor in a desired position;

adding an embedding medium to the well surrounding the tissue specimen;

placing a pre-chilled chuck on the well top opening, said chuck having a planar top, an opposing bottom, a plurality of sides and a plurality of flanges projecting downwardly from the chuck bottom, said chuck top having a plurality corrugations formed thereon, said chuck top being placed against said well top opening;

inverting and placing the cold mold with tissue specimen, embedding medium and chuck into a cryostat, wherein the chuck is placed on a cryostat cold rail, said the chuck flanges holding the chuck and mold in place on the cold rail;

bringing a cryostat anvil into contact with the cold mold bottom, wherein the tissue specimen and embedding medium are quickly frozen into a block;

removing the chuck and cold mold from the cryostat;

pouring a warming liquid against the cold mold bottom and releasing the block with attached chuck from the cold mold well;

cleaning and returning the cold mold to the cryostat for temperature maintenance;

making the chuck with attached block available for sectioning.

* * * * *